United States Patent [19]

Imaki et al.

[11] Patent Number: 4,916,147
[45] Date of Patent: Apr. 10, 1990

[54] 3-[(4-AROYL) PHENOXY (OR PHENYLTHIO)]-CYCLOPENTANECARBOXYLIC ACID ANALOGUES AND TREATMENT OF CEREBRAL EDEMA THEREWITH

[75] Inventors: Katsuhiro Imaki, Tsuzuki; Tadao Okegawa, Yawata; Yoshinobu Arai, Osaka, all of Japan

[73] Assignee: Ono Pharmaceutical Co., Ltd., Osaka, Japan

[21] Appl. No.: 887,772

[22] Filed: Jun. 21, 1986

[30] Foreign Application Priority Data

Jul. 19, 1985 [JP] Japan ................. 60-157990

[51] Int. Cl.$^4$ .................. C07D 257/04; A61K 31/41; A61K 31/12; C07C 49/23
[52] U.S. Cl. ................ 514/381; 514/568; 548/253; 562/460
[58] Field of Search ........... 562/460; 548/253; 514/381, 368

[56] References Cited

U.S. PATENT DOCUMENTS 3,398,188 8/1968 Schultz ................... 562/460
4,058,559 11/1977 Jones et al. ............. 562/460

*Primary Examiner*—David B. Springer
*Attorney, Agent, or Firm*—Sughrue, Mion, Zinn, Macpeak & Seas

[57] ABSTRACT

Novel compounds of the general formula:

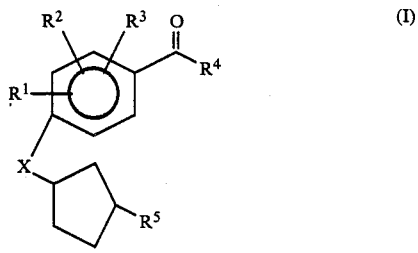

[wherein X represents an oxygen atom or sulfur atom, $R^1$, $R^2$ and $R^3$ represent a hydrogen atom, a halogen atom or an alkyl group of from 1 to 4 carbon atom(s) independently or a formula: $R^{3'}$

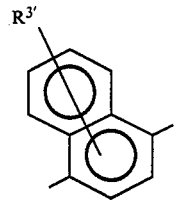

(wherein $R^{3'}$ represents a hydrogen atom or an alkyl group of from 1 to 4 carbon(s))

in place of a formula:

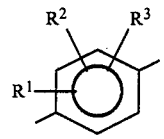

$R^4$ represents a general formula:

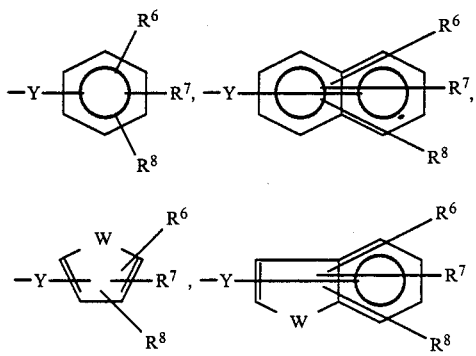

or $-N(R^9)_2$ (in which W represents an oxygen atom or sulfur atom, $R^6$, $R^7$ and $R^8$ represent a hydrogen atom, a halogen atom, a nitro group, an alkyl group of from 1 to 4 carbon atom(s), a hydroxy group or an alkoxy group of from 1 to 4 carbon atom(s) independently, each of $R^9$ represents a hydrogen atom, an alkyl group of from 1 to 4 carbon atom(s) or a phenyl group and Y represents a single bond or an alkylene group or an alkenylene group of from 1 to 4 carbon atom(s).), and $R^5$ represents a 5-tetrazolyl group or a general formula: $-COOR^{10}$ (in which $R^{10}$ represents a hydrogen atom or an alkyl group of from 1 to 4 carbon atom(s))]

and non-toxic salts possess inhibitory effect on cerebral edema.

6 Claims, No Drawings

3-[(4-AROYL) PHENOXY (OR PHENYLTHIO)]-CYCLOPENTANECARBOXYLIC ACID ANALOGUES AND TREATMENT OF CEREBRAL EDEMA THEREWITH

[INDUSTRIAL UTILITY]

This invention relates to novel 3-[(4-aroyl)phenoxy (or phenylthio)]cyclopentane carboxylic acid derivatives, processes for their preparation and treating agents for cerebral edema containing them as active ingredients.

[PRIOR ARTS]

Heretofore, 5-substituted-indan-1-one derivatives for the purpose of treatment of cerebral edema have been known. For example, in the specification of the European Patent Publication No. 47,011, it was proposed that the compounds represented by the general formula:

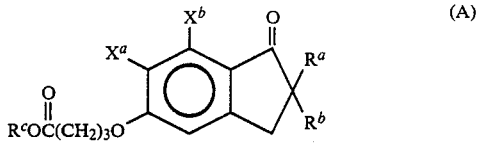

(wherein $X^a$ and $X^b$ represent a halogen atom, $R^a$ represents a lower alkyl group of from 1 to 6 carbon atoms(s), $R^b$ represents a hydrogen atom, a lower alkyl group of from 1 to 4 carbon atom(s), a cycloalkyl group of from 3 to 6 carbon atoms, a lower cycloalkyl-lower alkyl group of from 4 to 7 carbon atoms, or a phenyl and $R^c$ represents a hydrogen atom, a lower alkyl group of from 1 to 6 carbon atom(s) or a carboxy-lower alkyl group of from 2 to 6 carbon atoms.) and their salts may be used for treatment of cerebral edema.

In the general formula (A), the compound wherein $X^a$ and $X^b$ represent chlorine atoms, $R^a$ represents a methyl group, $R^b$ represents a cyclopentyl group and $R^c$ represents a hydrogen atom, i.e. (+)-4-[((2R)-2-cyclopentyl-2-methyl-6,7-dichloro-1-oxoindan-5-yl)oxy]butyric acid of the formula:

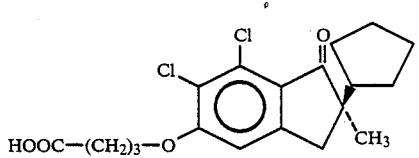

has been known as "DCPIB", and whose inhibitory effect on cerebral edema was described in detail in Journal of Medicinal Chemistry, Vol. 25 (No. 5), 567 (1982).

And further, it is described in the specification of European Pat. No. 27,948 that these kinds of 3-oxo-3H-fluorene derivatives have the inhibitory effect on cerebral edema.

But the chemical structures of these compounds are much different from that of compounds of this invention.

And further, compounds whose cyclopentanone of their indane skeleton are opened were described in the specification of the British Pat. No. 1,548,729 and the U.S. Pat. No. 3,758,506. For example, in the specification of the British Pat. No. 1,548,729, it was proposed that the compounds represented by the general formula:

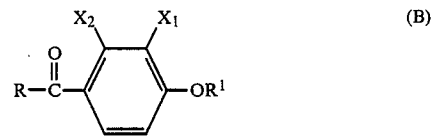

(wherein R represents a phenyl, a substituted phenyl or a naphthyl group, R' represents a formula: —CH$_2$COOH or a methyltetrazolyl group, and $X_1$ and $X_2$ represent a halogen atom or a lower alkyl group respectively, or a naphthalene ring when both of them and the phenyl ring substituted by them join with one another.) However, in the symbol $R^1$ in formula (B), the group to which the carboxy or tetrazolyl group is attached is methylene group. On the other hand, the said group of our invention is cyclopentylene group. Therefore, there is much different in chemical structure between compounds of formula (B) and those of our invention. As the main activity of the compounds are diuresis and reducing blood pressure, therefore these compounds are much different from the compounds of the present invention described hereafter.

[PURPOSE]

The purpose of the present invention is the proposal of the novel compounds which have inhibitory effect on cerebral edema.

[MEANS TO ACCOMPLISH THE PURPOSE]

We proposed before, the compounds that the trimethylene group between an indanyloxy group and a carboxy group in a side chain of DCPIB was replaced by a cyclopentylene group (See U.S. patent application Ser. No. 792,399/85). It was confirmed that they have the inhibitory effect on cerebral edema. In these compounds, we left a cyclopentylene group as it is, deleted the asymmetric carbon atom of an indane skeleton by way of opening a cyclopentanone part of an indane skeleton and added to the carbonyl group an aroyl group such as a phenyl group, a naphthyl group or various heterocyclic groups.

The compounds are novel, their structure is unobvious and as a result of the examination of their pharmacological activity, it has now been found that they have an inhibitory effect on cerebral edema, and then completed the invention.

[CONSTITUTION OF THE INVENTION]

Accordingly, the present invention relates to novel compounds of the general formula:

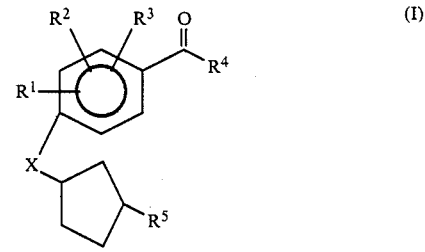

[wherein X represents an oxygen atom or a sulfur atom, $R^1$, $R^2$ and $R^3$ represent a hydrogen atom, a halogen atom or an alkyl group of from 1 to 4 carbon atom(s) independently or a formula:

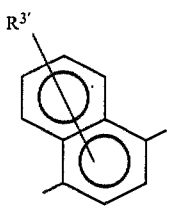

(wherein R³' represents a hydrogen atom, a halogen atom or an alkyl group of from 1 to 4 carbon atom(s).) in place of a formula:

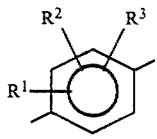

R⁴ represents a general formula:

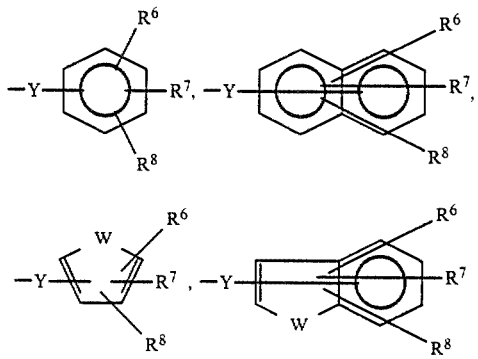

or —N(R⁹)₂ (in which W represents an oxygen atom or sulfur atom, R⁶, R⁷ and R⁸ represent a hydrogen atom, a halogen atom, a nitro group, an alkyl group of from 1 to 4 carbon atom(s), a hydroxy group or an alkoxy group of from 1 to 4 carbon atom(s) independently, each of R⁹ represents a hydrogen atom, an alkyl group of from 1 to 4 carbon atom(s) or a phenyl groups and Y represents a single bond or an alkylene group or an alkenylene group of from 1 to 4 carbon atom(s)), and R⁵ represents a 5-tetrazolyl group or a general formula: —COOR¹⁰ (in which R¹⁰ represetns a hydrogen atom or an alkyl group of from 1 to 4 carbon atom(s).)] and their non-toxic salts when R⁵ represents a carboxy group or a 5-tetrazolyl group, processes for their preparation and treating agents for cerebral edema containing them as active ingredients.

It is to be understood that alkyl, alkylene, alkenylene and alkoxy groups within the definitions of various symbols in this specification and the accompanying claims may be straight or branched-chain.

In the structural formulae in this specification, the broken line (---) indicates the α-configuration, the bold line (—) indicates the β-configuration, the wavy line (∼) indicates the α-configuration or the β-configuration or a mixture thereof.

In the general formula (I), examples of the halogen atoms represented by R¹, R² and R³ are fluorine, chlorine, bromine and iodine atoms, the alkyl groups of from 1 to 4 carbon atom(s) are methyl, ethyl, propyl, butyl groups and isomers thereof and the alkoxy groups of from 1 to 4 carbon atom(s) are methoxy; ethoxy, propyloxy, butoxy groups and isomers thereof. Preferably at least one of R¹, R² and R³ represents a hydrogen atom and the other one or two represent(s) a halogen atom or a methyl group, and more preferably all of them represent hydrogen atoms or one or two chlorine atom(s) is (are) substituted. And further an unsubstituted naphthyl group is preferable.

In the general formula (I), examples of the halogen atoms, the alkyl and alkoxy groups of from 1 to 4 carbon atom(s) represented by R⁶, R⁷ and R⁸ in R⁴ are the same atoms and groups represented by R¹, R² and R³. Preferably all of R⁶, R⁷ and R⁸ represent hydrogen atoms or one or two of them is (are) fluorine atom, chlorine atom, methyl group, methoxy group, hydroxy group, or nitro group.

Examples of the alkylene groups of from 1 to 4 carbon atom(s) represented by Y are methylene, ethylene, trimethylene, tetramethylene groups and isomers thereof and examples of the alkenylene groups are vinylene, propenylene, butenylene groups and isomers thereof. A single bond, a methylene and vinylene group are preferable.

Examples of the alkyl groups represented by R⁹ are methyl, ethyl, propyl, butyl groups and isomers thereof.

The preferred R⁴ are the following groups of the formula:

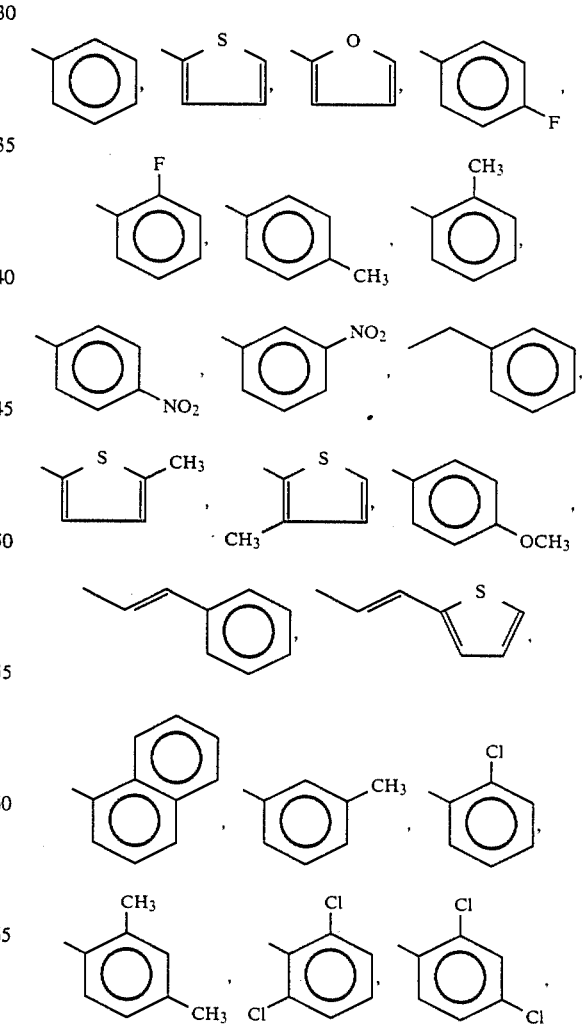

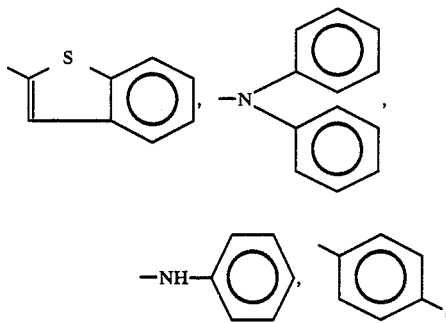

In the general formula (I), examples of the alkyl groups represented by $R^{10}$ in $R^5$ are methyl, ethyl, propyl, butyl groups and isomers thereof.

The preferred $R^5$ are carboxy, methoxycarbonyl and 5-tetrazolyl groups.

As for the stereo-configuration of the carbon atoms at the 1- and 3-positions of a cyclopentylene group, (1S,3S), (1R,3R), (1S,3R) and (1R,3S) are also preferable, and (1S,3S) and (1R,3R) which are composed a trans-configuration each other, are more preferable and above all (1S,3S) is the most preferable.

Preferred compounds of the general formula (I) of the present invention are, for example, as follows:

(1S,3S)-3-[(2,3-dichloro-4-benzoyl)phenoxy]cyclopentanecarboxylic acid, (1R,3R)-3-[(2,3-dichloro-4-benzoyl)phenoxy]cyclopentanecarboxylic acid, (±)-trans-3-[(2,3-dichloro-4-benzoyl)phenoxyl]cyclopentanecarboxylic acid, (1S,3S)-3-[{2,3-dichloro-4-(2-thenoyl)}phenoxy]cyclopentanecarboxylic acid, (1R,3R)-3-[{2,3-dichloro-4-(2-thenoyl)}phenoxy]cyclopentanecarboxylic acid, (±)-trans-3-[{2,3-dichloro-4-(2-thenoyl)}phenoxy]cyclopentanecarboxylic acid, (1S,3S)-3-[{2,3-dichloro-4-(2-furoyl)}phenoxy]cyclopentanecarboxylic acid, (1S,3S)-3-[{2,3-dichloro-4-(4-fluorobenzoyl)}phenoxy]cyclopentanecarboxylic acid, (1S,3S)-3-[{2,3-dichloro-4-(2-fluorobenzoyl)}phenoxy]cyclopentanecarboxylic acid, (1S,3S)-3-[{2,3-dichloro-4-(4-methylbenzoyl)}phenoxy]cyclopentanecarboxylic acid, (1S,3S)-3-[{2,3-dichloro-4-(2-methylbenzoyl)}phenoxy]cyclopentanecarboxylic acid, (1S,3S)-3-{[2,3-dichloro-4-(4-nitrobenzoyl)}phenoxy]cyclopentanecarboxylic acid, (1S,3S)-3-[{2,3-dichloro-4-(3-nitrobenzoyl)}phenoxy]cyclopentanecarboxylic acid, (1S,3S)-3-[(2,3-dichloro-4-phenylacetyl)phenoxy]cyclopentanecarboxylic acid, (1S,3S)-3-[{2,3-dichloro-4-(5-methyl-2-thenoyl)}phenoxy]cyclopentanecarboxylic acid, (1S,3S)-3-[{2,3-dichloro-4-(3-methyl-2-thenoyl)}phenoxy]cyclopentanecarboxylic acid, (1S,3S)-3-[{2,3-dichloro-4-(4-methoxybenzoyl)}phenoxy]cyclopentanecarboxylic acid, (1S,3S)-3-[(2,3-dichloro-4-cinnamoyl)phenoxy]cyclopentanecarboxylic acid, (1S,3S)-3-[{2,3-dichloro-4-(3-(2-thenoyl)acryloyl)}phenoxy]cyclopentanecarboxylic acid, (1S,3S)-3-[{2,3-dichloro-4-(1-naphthoyl)}phenoxy]cyclopentanecarboxylic acid, (1S,3S)-3-[{2,3-dichloro-4-(3-methylbenzoyl)}phenoxy]cyclopentanecarboxylic acid, (1S,3S)-3-[{2,3-dichloro-4-(2-chlorobenzoyl)}phenoxy]cyclopentanecarboxylic acid, (1S,3S)-3-[{2,3-dichloro-4-(2,4-dimethylbenzoyl)}phenoxy]cyclopentanecarboxylic acid, (1S,3S)-3-[{2,3-dichloro-4-(2,6-dichlorobenzoyl)}phenoxy]cyclopentanecarboxylic acid, (1S,3S)-3-[(2-chloro-4-benzoyl)phenoxy]cyclopentanecarboxylic acid, (1S,3S)-3-[(3-chloro-4-benzoyl)phenoxy]cyclopentanecarboxylic acid, (1S,3S)-3-[(2,6-dichloro-4-benzoyl)phenoxy]cyclopentanecarboxylic acid, (1S,3S)-3-[(3-fluoro-4-benzoyl)phenoxy]cyclopentanecarboxylic acid, (1S,3S)-3-[(2-fluoro-4-benzoyl)phenoxy]cyclopentanecarboxylic acid, (1S,3S)-3-(2,6-dimethyl-4-benzoylphenoxy)cyclopentanecarboxylic acid, (1S,3S)-3-[4-(2,4-dichlorobenzoyl)phenoxy]cyclopentanecarboxylic acid, (1S,3S)-3-[2,6-dimethyl-4-(2,4-dichlorobenzoyl)phenoxy]cyclopentanecarboxylic acid, (1S,3S)-3-[2,6-dimethyl-4-(1-naphthoyl)phenoxy]cyclopentanecarboxylic acid, (1S,3S)-3-[3-chloro-4-(1-naphthoyl)phenoxy]cyclopentanecarboxylic acid, (1S,3S)-3-[2,3-dichloro-4-(2-benzo[b]thenoyl)phenoxy]cyclopentanecarboxylic acid, (1S,3S)-3-[2,3-dichloro-4-(p-hydroxybenzoyl)phenoxy]cyclopentanecarboxylic acid, (1S,3S)-3-(4-benzoyl-1-naphthoxy)cyclopentanecarboxylic acid, (1S,3S)-3-[(2,3-dimethyl-4-benzoyl)phenoxy]cyclopentanecarboxylic acid, (1S,3S)-3-(2,3-dichloro-4-diphenylcarbamoylphenoxy)cyclopentanecarboxylic acid, (1S,3S)-3-(2,3-dichloro-4-phenylcarbamoylphenoxy)cyclopentanecarboxylic acid, (1S,3S)-3-(4-benzoylphenoxy)cyclopentanecarboxylic acid, (1S,3S)-3-[4-(2-thenoyl)phenoxy]cyclopentanecarboxylic acid, (1S,3S)-3-(4-benzoyl-2,3-dichlorophenylthio)cyclopentanecarboxylic acid, and their methyl esters, their non-toxic salts, the compounds replaced by 5-tetrazolyl group for carboxy group and their non-toxic salts.

[PROCESSES FOR THE PREPARATION]

(1) The compounds of the present invention represented by the general formula (I) can be produced by the following scheme.

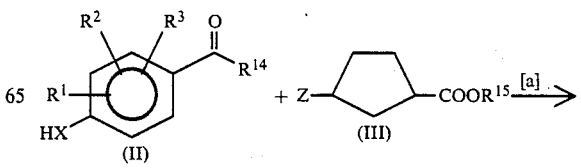

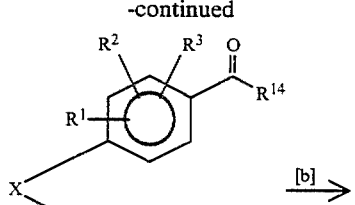

(Ia)

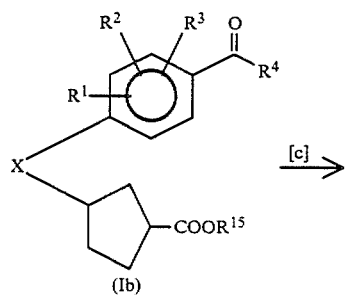

(Ib)

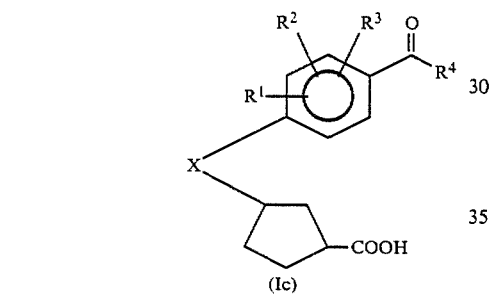

(Ic)

[Wherein X represents an oxygen atom or a sulfur atom, $R^1$, $R^2$ and $R^3$ represent a hydrogen atom, a halogen atom or an alkyl group of from 1 to 4 carbon atom(s) independently or a formula:

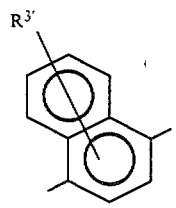

(wherein $R^{3'}$ represents a hydrogen atom, a halogen atom or an alkyl group of from 1 to 4 carbon atom(s).) in place of the general formula:

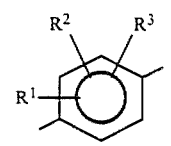

$R^{14}$ represents the general formula:

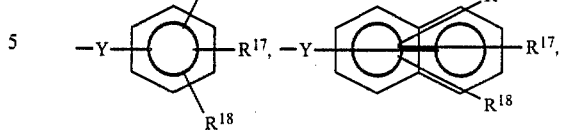

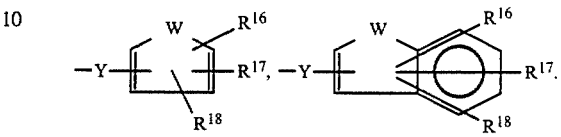

or $-N(R^9)_2$ (in which $R^{16}$, $R^{17}$ and $R^{18}$ represent a hydrogen atom, a halogen atom, an alkyl or an alkoxy group of from 1 to 4 carbon atom(s) or a nitro group independently, each of $R^9$ represents a hydrogen atom, an alkyl group of from 1 to 4 carbon atom(s) or a phenyl group, Y represents a single bond or an alkylene or alkenylene group of from 1 to 4 carbon atom(s) and W represents an oxygen atom or a sulfur atom.) $R^{15}$ represents an alkyl group of from 1 to 4 carbon atom(s), Z represents a halogen atom or a substituted or unsubstituted alkylsulfonyloxy or arylsulfonyloxy group such as methanesulfonyloxy or p-toluenesulfonyloxy group and $R^4$ represents a general formula:

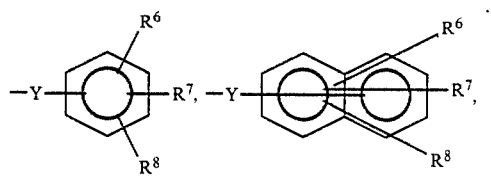

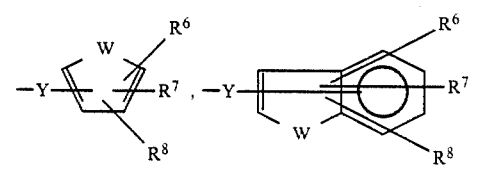

or $-N(R^9)_2$ (wherein $R^6$, $R^7$ and $R^8$ represent a hydrogen atom, a halogen atom, a nitro group, an alkyl group of from 1 to 4 carbon atom(s), a hydroxy group or an alkoxy group of from 1 to 4 carbon atom(s) and the other symbols are as hereinbefore defined.)]

The step [a] is an additional reaction and may be carried out by reacting the compounds of the general formula (II) and those of the general formula (III), in the presence of a base, e.g. such a hydride of alkali metal as sodium hydride, such an alkoxide of alkali metal as sodium ethoxide or such a carbonate or hydroxide of alkali metal as potassium carbonate or sodium hydroxide, in such an inert organic solvent as tetrahydrofuran, dimethylformamide, dimethylsulfoxide, hexamethylphosphoramide or dimethoxyethane or the mixture thereof, at a temperature from 0° C. to a reflux temperature of the reaction mixture, preferably at a temperature from room temperature to 60° C. The step [b] may be carried out, if desired, when $R^{16}$, $R^{17}$ or $R^{18}$ in $R^{14}$ represents a nitro group and by known methods for the conversion of a nitro group into a hydroxy group. Namely, it may be carried out by reacting the compound substituted by a nitro group in the general formula (Ia) with an oxime compound such as acetoaldoxime in such an inert organic solvent as dimethylformamide, in the presence of such a base as sodium hydroxide, at below room temperature preferably at 0° C. The obtained phenol derivative in this way is converted into an derivative substituted by an alkoxy group by known methods, if desired. Namely it may be carried out that the phenol derivative is reacted by using such an agent for alkylation as alkyl halide, in such an inert organic solvent as dimethylformamide, in the presence of such a base as sodium hydride, at a temperature from 80° C. to room temperature. And the step [c] is a saponification reaction and may be carried out by the reaction in the presence of a solvent soluble in water, for example tetrahydrofuran or an alkanol of from 1 to 4 carbon atom(s) (e.g. methanol), using an aqueous solution of a hydroxide or carbonate of an alkali metal, for example, lithium, sodium or potassium, at a temperature from 0° C. to a room temperature.

(2) (1) The compound of the general formula (II) used as a starting material can be prepared by the following scheme, in the case that X represents an oxygen atom and $R^{14}$ represent a group except for amino group.

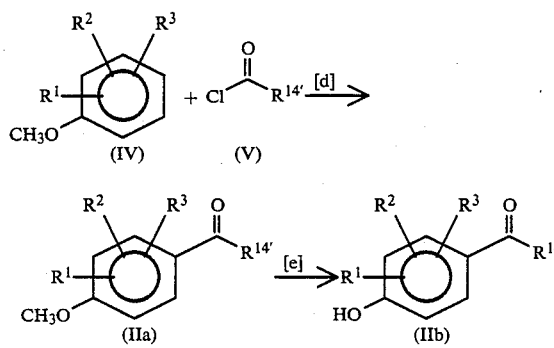

[Wherein $R^{14'}$ represents same group except for the general formula $—N(R^9)_2$ in the general formula of $R^{14}$. The other symbols are the same meaning as described hereinbefore.]

The step [d] is Friedel-Crafts acylation and the step [e] is eliminating reaction of methyl group, and may be prepared by the method described in the specification of the British Pat. No. 1,548,729.

(2) The compound of the general formula (II) used as a starting material can be prepared by the following scheme, in the case of X represents an oxygen atom and $R^{14}$ represents $—N(R^9)_2$ ($R^9$ is as hereinbefore defined.).

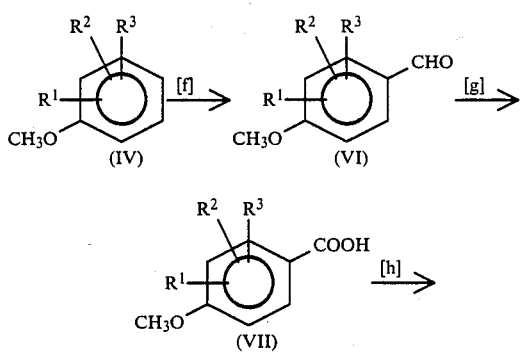

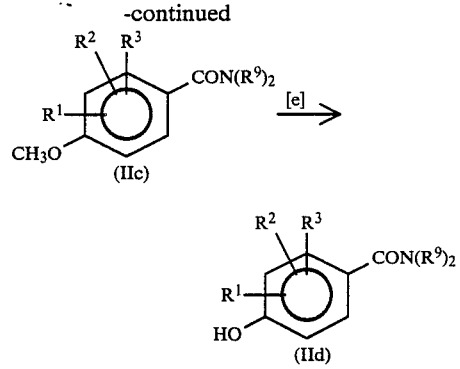

[wherein, all the symbols are the same meaning as described hereinbefore.]

The step [f] is Friedel-Crafts reaction, may be carried out as the step [d], hereupon as Lewis acid to use titanium chloride is preferably.

The step [g] is oxidation to convert aldehyde into carboxylic acid, some methods have been known, for example, it may be carried out to use potassium permanganate or chromic acid as oxidizing agent at a temperature of from 0° C. to 40° C. preferably at room temperature in aqueous solution. And further as the other oxidation reaction may be carried out to use chromium trioxide-pyridine complex (for example Collins' reagent), Jones' reagent or chromic acid solution (prepared from chromium trioxide, manganese sulfate, sulfuric acid and water) or oxalyl chloride and dimethylsulfoxide [i.e. Swern oxidation] etc. The oxidation using Collins' reagent may be conducted in a halogenated hydrocarbon such as chloroform, methylene chloride or carbon tetrachloride at a temperature of from 0° C. to room temperature. The oxidation using Jones' reagent may be generally conducted at a temperature below room temperature. The Swern oxidation may be conducted by reaction in a halogenated hydrocarbon such as chloroform or methylene chloride at a temperature of from $-50°$ C. to $-60°$ C., and then quenched by triethylamine. Hereupon to be conducted by the former method is preferably.

The step [h] is reaction of forming amide-bond. Reactions to form amide-bond from acid and amine are well known, for example, (A) by the method with using mixed acid anhydride
(B) by the method with using acid halide
(C) by the method with using DCC etc.

Concrete description of these methods described above are as follows:

(A) method with using mixed acid anhydride may be carried out, for example, an acid of the general formula (VII) is reacted with an acid halide (pivaloyl chloride, thionyl chloride, tosyl chloride, mesyl chloride, oxalyl chloride etc.) or an acid derivative (ethyl chloroformate, isobutyl chloroformate etc.) in an inert organic solvent (chloroform, methylene chloride, diethyl ether, THF etc.) or without solvents in the presence of tertiary amine (pyridine, triethylamine, picoline etc.), at from 0° C. to 40° C. to give a mixed acid anhydride. The obtained acid mixed anhydride and an amine of the general formula described $HN(R^9)_2$ are reacted in an inert organic solvent (described above), at from 0° C. to 40° C.

(B) method with using acid halide may be carried out, for example, an acid of the general formula (VII) is reacted with acid halide in an inert organic solvent (described in above) or without solvents at from −20° C. to a refluxing temperature to give an acid halide. The obtained acid halide and an amine of the general formula described $HN(R^9)_2$ are reacted in an inert organic solvent (described above) in the presence or absence of tertiary amine (described above) at from 0° C. to 40° C.

(C) method with using DCC may be carried out, for example, an acid of the general formula (VII) and an amine of the general formula described $HN(R^9)_2$ are reacted in an inert organic solvent (described above) or without solvents in the presence or absence of tertiary amine (described above) using with DCC (dicyclohexylcarbodiimide) at from 0° C. to 40° C.

Preferably, the reactions (A), (B) and (C) described above are carried out in an atmosphere of inert gas (argon, nitrogen etc.) on anhydrous condition.

From the compound obtained in this way, of the general formula (IIc), the compound of the general formula (IId) may be obtained by eliminating reaction of methyl group as the same reaction as the step [e].

(3) The compound of the general formula (II) used as a starting material can be prepared by the method excepting Friedel-Crafts reaction, in the case that X represents an oxygen atom and $R^{14}$ represent other group exclusive of amino group. For example, it can be prepared by the following scheme;

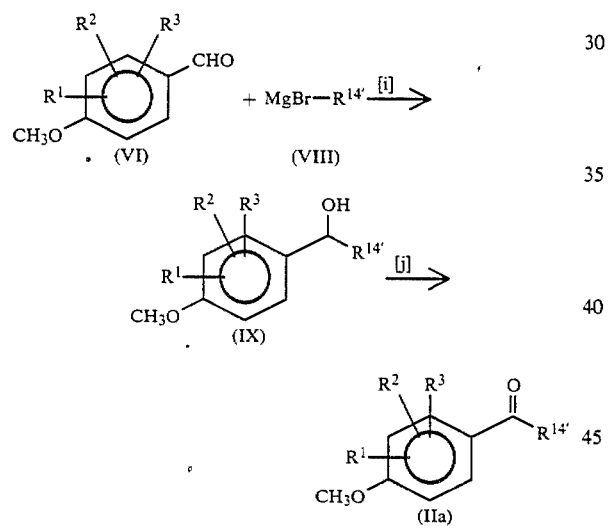

(wherein, all the symbols are the same meaning as described hereinbefore.)

The step [i] is Grignard additional reaction and it may be carried out by known methods.

The step [j] is oxidation reaction that hydroxy group is converted into oxo group, and this step may be carried out by the same reaction as the step [g]. Hereupon the oxidation reaction using Collins' reagent, the oxidation reaction using Jones' reagent or the Swern oxidation is preferably.

(4) The compound of the general formula (II) used as a starting material can be prepared from the compounds of the general formula (IIb) and (IId) by the method described in the specification of the U.S. patent application Ser. No. 792,399/85, in the case that X represents sulfur atom.

(3) The compound of the general formula (III) used as the other starting material can be prepared from 3-oxocyclopentanecarboxylic acid by the method described in the specification of the U.S. patent application Ser. No. 792,399/85.

(4) Compounds that the carboxy group in the compound of the formula (Ic) is replaced to tetrazolyl group may be prepared by the following scheme:

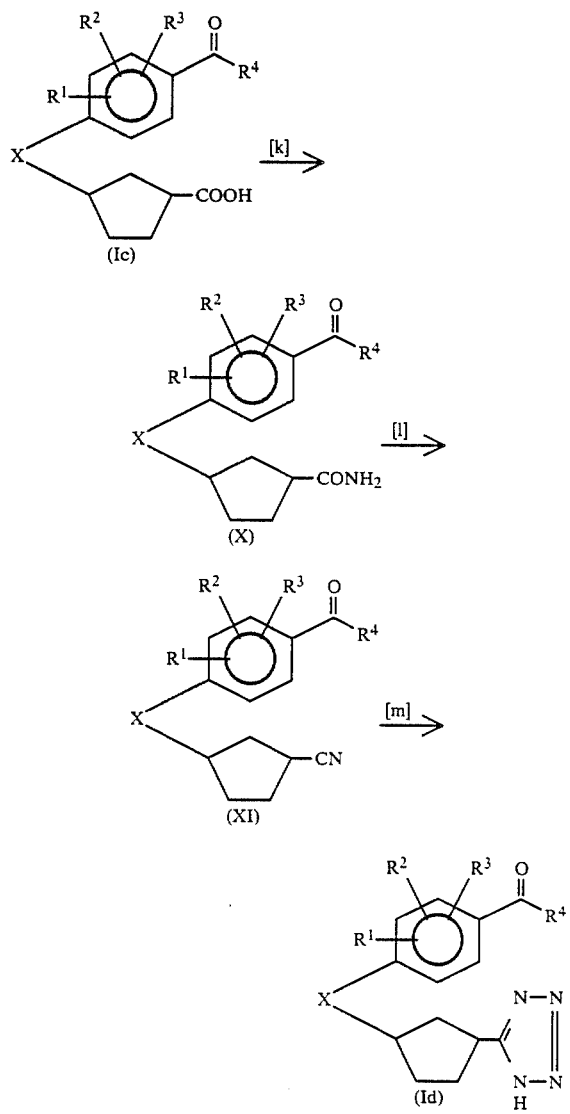

(wherein, all the symbols are the same meaning as described hereinbefore.)

The step [k] is reaction to form amide bond, it may be carried out by the same method as the step [h].

The step [l] is dehydration reaction, and it may be carried out by converting amide into nitrile. For example, this step may be carried out to use thionyl chloride etc. in an inert organic solvent such as dimethylformamide at from room temperature to a refluxing temperature of the solvent used.

The step [m] is a reaction to form a 5-tetrazolyl group by reacting a cyano group with an azide. For example, it may be carried out by using an azide (sodium azide, lithium azide, potassium azide etc.) in the presence of a weak acid (pyridium chloride, ammonium chloride, dimethylaniline hydrochloride etc.) in an inert organic solvent (dimethylformamide, N-methylpyrolidone etc.) on anhydrous condition by heating.

The compounds of the general formula (Ic) and (Id) may be converted into salts by known methods.

The salts are preferably non-toxic and water-soluble. Suitable salt are, for example, a salt of such an alkali metal as sodium or potassium, a salt of such an alkaline earth metal as calcium or magnesium, or an ammonium salt or a non-toxic amine salt, for example, such a tetraalkylammonium salt as tetramethylammonium salt or such an organic amine salt as methylamine, dimethylamine, cyclopentylamine, benzylamine, phenetylamine, piperidine, monoethanolamine, diethanolamine, tris(hydroxymethyl) aminomethane, lysine, arginine or N-methyl-D-glucamine salts.

[EFFECT]

The compounds of the general formula (I) and their non-toxic salts have a potent inhibitory effect on development of cerebral edema.

A group of diseases which cause cerebral edema is such diseases of cerebral ischemia as cerebral blood vascular damage (e.g. cerebral infarction, cerebral thrombosis), decrease of cerebral blood flow, cerebral ischemia, cerebral anoxia or spinal cord damage. In these diseases, because of the deficiency in oxygen supplied to organs, the level of energy production decreases, and then it becomes impossible to maintain the exchange reaction of $Na^+ \longleftrightarrow K^+$ across the cell membrances by ATPase (adenosinetriphosphatase), and further the intracellular concentration of $Na^+$ and $Cl^-$ increases. Accordingly, because extracellular water is taken into the cell, cerebral edema is developed. Another group of diseases which cause cerebral edema is such diseases that brings about the physical compression as cephalic trauma or cerebral tumor. In these diseases, it has been also considered that a damage in cellular function by physical compression leads $Na^+$ influx followed by water influx into the cells, and then edema is developed.

The compounds of the general formula (I) and their non-toxic salts inhibit the influx of $Na^+$ and $Cl^-$, and of water into cells and therefore potently inhibit the formation of cerebral edema. Accordingly, they are useful for the prevention of and the treatment of cerebral edema caused by any diseases as mentioned above.

The inhibitory effect on cerebral edema of the compounds of the present invention is confirmed by the following screening test.

THE INHIBITION TEST ON CEREBRAL EDEMA USING ORGAN SLICE OF CAT CEREBRAL CORTEX

The test was carried out by the method described in Journal of Medicinal Chemistry, Vol. 25 (No. 5), 567 (1982).

That is, brain was isolated from a cat weighing 2~4 kg, slices of about 1 mm in thickness was prepared, the white matter substance was removed, and the gray matter substance (100~150 mg a test) was used for a sample. The sample was added to the following incubation medium and incuvated for 50 minutes at 37° C. After the incubation, the sample was immediately weighed again to determine the swelling weight of the sample.

INCUBATION MEDIUM (osmotic pressure, 280~290 mOsm/l)

1. Hepes Buffer (pH 7.4)... 2.365 ml

| | |
|---|---|
| glucose | 10 mM |
| $CaCl_2$ | 1.3 mM |
| $MgSO_4$ | 1.2 mM |
| $KH_2PO_4$ | 1.2 mM |
| Hepes | 20 mM |
| NaCl | 122 mM |
| KCl | 20 mM | adjusted to pH 7.4 by NaOH 2. test compounds [dissolved in the presence of tris(hydroxymethyl) aminomethane] or water... 0.01 ml 3. 0.2M $NaHCO_3$ (dissolved by Hepes Buffer, giving the final concentration of 10 mM in medium) or Hepes Buffer... 0.125 ml The test was carried out by using $NaHCO_3$ as a stimulating agent of swelling.

(A) A percentage of swelling when a slice sample was added to incubation medium comprising Hepes Buffer, water and $NaHCO_3$ (defined as maximum of swelling).

(B) A percentage of swelling when a slice sample was added to incubation medium comprising Hepes Buffer and water (defined as maximum inhibition of swelling).

(C) A percentage of swelling when a slice sample was added to incubation medium comprising Hepes Buffer, the test compounds in various concentrations and $NaHCO_3$.

Above-mentioned (A), (B) and (C) were determined. Inhibition percentage of the test compounds was caliculated by the following equation:

$$\text{inhibition \%} = \frac{(A) - (C)}{(A) - (B)} \times 100$$

$IC_{50}$ value was determined by dose-response curve as a concentration in which inhibition percentage was 50.

The results are shown Table I. And further, percentages of swelling of (C) was counted, in the case that concentration of test compound of (C) was $10^{-8}$M, and inhibition of swelling at the concentration of $10^{-8}$M was determined by percentages of swelling of both (A) and (B).

The results are shown in Table II.

TABLE I

| Inhibitory effect on cerebral edema | |
|---|---|
| example No. of test compound | inhibitory activity cerebral edema ($IC_{50}$, M) |
| Ex. 1 | $5.5 \times 10^{-9}$ |
| Ex. 1 - 3 | $2.2 \times 10^{-9}$ |
| Ex. 1 - 8 | $2.6 \times 10^{-9}$ |
| Ex. 1 - 19 | $4.1 \times 10^{-9}$ |
| Ex. 1 - 25 | $3.0 \times 10^{-9}$ |

TABLE II

| Inhibitory activity on celebral edema | |
|---|---|
| example No. of test compound | a percentage of inhibition of swelling at $10^{-8}$ M (%) |
| 1 - 8 | 82 |
| 1 - 12 | 52 |
| 1 - 13 | 36 |
| 1 - 19 | 90 |
| 1 - 20 | 78 |
| 1 - 25 | 100 |

TABLE II-continued

| | Inhibitory activity on celebral edema |
|---|---|
| example No. of test compound | a percentage of inhibition of swelling at $10^{-8}$ M (%) |
| 4 | 41 |

And further, the toxicity of compound of this invention is enough low, and therefore, it can be confirmed to be able to use enough safety as drug.

For example, in the acute toxicity test in mice by intravenous administration, the mortality of compound of example 1 and 1-3 are 0/6 and 0/6 at the dose of 100 mg/kg and are 6/6 and 4/6 at the dose of 200 mg/kg, respectively.

Accordingly the compound of this invention is useful for prevention and treatment for cerebral edema in mammal, specifically human being in those.

For the purpose of the prevention and the treatment for cerebral edema, the compounds of the general formula (I) or non-toxic salts thereof may normally be administered systemically or partially, usually by oral or parenteral administration. The dose to be administered is determined depending upon age, body weight, symptom, the desired therapeutic effect, the route of administration, and the duration of the treatment etc. In the human adult, the doses per person for one time are generally between 1 mg and 1 g, by oral administration up to several times per day, and between 100 μg and 100 mg, by parenteral administration. (preferably by intravenous administration) up to several times per day.

As mentioned above, the doses to be used depend on various conditions. Therefore, there are cases in which doses lower than the ranges specified above and doses greater than the ranges specified above, may be used.

Solid compositions according to the present invention for oral administration include compressed tablets, dispersible powders and granules. In such solid compositions, one or more of the active compound(s) is, or are, admixed with at least one inert diluent such as lactose, mannitol, glucose, hydroxypropyl cellulose, microcrystalline cellulose, starch, polyvinyl-pyrrolidone or magnesium metasilicate aluminate. The compositions may also comprise, as is normal practice, additional substances other than inert diluents e.g. lubricating agents such as magnesium stearate, and, disintegrating agents such as cellulose calcium gluconate. The tablets or pills may, if desired, be made into gastric film-coated or enteric film-coated tablets or pills, such as sugar-coated, gelatin-coated, hydroxypropylcellulose-coated or hydroxypropylmethylcellulose phthalate-coated tablets or pills; two or more layers may be used. The compositions for oral administration also include capsules of absorbable material such as gelatin.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other compositions for oral administration include spray compositions which may be prepared by known methods and which comprise one or more of the active compound(s).

Preparations for injection according to the present invention for parenteral administration include sterile aqueous or non-aqueous solutions, suspensions or emulsions. Example of aqueous solvents or suspending media are distilled water for injection and physiological salt solution. Examples of non-aqueous solvents or suspending media are propylene glycol, polyethylene glycol, vegetable oils such as olive oil, alcohols such as ethanol, Polysorbate 80 (registered Trade Mark). These compositions may also include adjuvants such as preserving, wetting, emulsifying and dispersing agents. They may be sterilized, for example, by filtration through a bacteria-retaining filter, by incorporation of sterilizing agents in the compositions or by irradiation. They may also be manufactured in the form of sterile solid compositions which can be dissolved in sterile water or some other sterile injectable medium immediately before use.

Other compositions for parenteral administration include liquids for external use, and endermic liniments such as ointments, suppositories for rectal administration and pessaries for vaginal administration which comprise one or more of the active compound(s) and may be prepared by known methods.

The following Reference Examples and Examples illustrate the preparation of compounds of the present invention, however, the present invention is not restricted to them. In the Reference Examples and Examples, "TLC", "NMR", "IR" and "MS" represent "Thin layer chromatography", "Nuclear magnetic resonance spectrum", "Infrared absorption spectrum" and "Mass spectrum", respectively. The solvents in parenthesis specified in chromatographic separations show the developing solvents. Except when specified otherwise, infrared absorption spectra were recorded by the liquid film method and nuclear magnetic resonance spectra were recorded in deuterochloroform (CDCl$_3$) solution. In the structural formulae, "Ms" represents "methanesulfonyl group (mesyl group)".

[REFERENCE EXAMPLE 1]

(1S,3R)-3-mesyloxycyclopentanecarboxylic acid tert-butyl ester

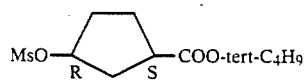

24 ml of tert-butylalcohol and 2.44 g of 4-dimethylaminopyridine were added to a solution of 25.6 g of (1S)-3-oxocyclopentanecarboxylic acid in 140 ml of methylene chloride.

The mixture was cooled to 0°~1° C. and 45.32 g of dicyclohexylarbodiimide dissolved in 120 ml of methylene chloride was added to the mixture. The mixture was stirred for three hours at 2° C.

500 ml of ether was added to the reaction mixture and precipitate was filtered off. The solution was concentrated under reduced pressure.

The residue was purified by column chromatography on silica-gel (n-hexane: ethyl acetate=4:1) to give 34.39 g of tert-butyl ester compound.

529 mg of sodium borohydride was added to a solution of 2.601 g of the obtained tert-butyl ester compound dissolved in 15 ml of methanol cooled with ice.

The solution was stirred for twenty minutes.

The reaction mixture was concentrated under reduced pressure and methanol in this solution was distilled off. The residue was dissolved in ethyl acetate.

After washing and drying, the solution was concentrated under reduced pressure and the solution was purified by column chromatography on silica-gel (methylene chloride: ethyl acetate=10:1) to get 1.866 g of cis compound and 496 mg of trans compound.

In an atmosphere of argon, 46.7 ml of triethylamine and 24 ml of mesyl chloride was added to a solution of 48.1 g of cis compound in 500 ml of methylene chloride at −20° C. At the same temperature, the solution was stirred for ten minutes.

The reaction mixture was poured into 500 ml of ice-water. The organic layer was washed with a saturated aqueous solution of sodium chloride. The solution was dried and concentrated under reduced pressure. The residue was dissolved in ether. The solution was washed with water and a saturated aqueous solution of sodium chloride and dried and concentrated under reduced pressure to give 66.73 g of the title compound having the following physical data.

TLC (methylene chloride: ethyl acetate=10:3): Rf=0.74;

NMR: δ 5.13 (1H, m), 3.0 (3H, m), 2.74 (1H, m), 2.26 (2H, m), 2.16∼1.84 (4H, m), 1.44 (9H, S);

MS: m/Z 264, 249, 209, 191, 165, 113, 95.

By the same procedure as described in Reference Example 1, (1R,3S)-3-mesyloxychlopentanecarboxylic acid tert-butyl ester and (dl)-cis-3-mesyloxycyclopentanecarboxylic acid tert-butyl ester was obtained.

[REFERENCE EXAMPLE 2]

Synthesis of 2,3-dichloro-4-benzoylphenol

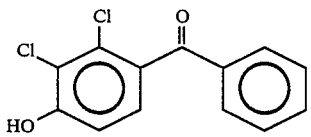

1.4 g of benzoyl chloride was added to 1.77 g of 2,3-dichloroanisole (on the market) in 30 ml of methylene chloride.

The mixture was cooled to 0° C. and 1.33 g of aluminium chloride was added to. The mixture was reacted for thirty minutes at 0° C., and further for six hours at the room temperature.

The reaction mixture was poured into the mixture of concentrated hydrochloric acid and ice-water. The solution was extracted with methylene chloride.

The extract was washed with a 10% aqueous solution of sodium hydroxide and a saturated aqueous solution of sodium chloride. The solution was dried and then concentrated under reduced pressure and then purified by recrystallization (n-hexane: ethyl acetate=10:1→4:1) to give 1.187 g of 2,3-dichloro-4-benzoylanisole.

4.3 g of pyridinehydrochloride salt was added to 500 mg of the obtained anisole compound. The mixture was stirred for two hours at 180° C., and poured into ice-water and extracted with ether.

The extract was washed with water and saturated an aqueous solution of sodium chloride and dried and concentrated under reduced pressure to give 470 mg of the title compound as crude product.

[EXAMPLE 1]

Synthesis of (1S,3S)-3-[(2,3-dichloro-4-benzoyl)phenoxy]cyclopentanecarboxylic acid

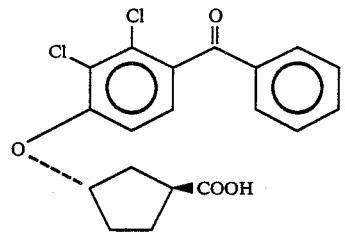

37.5 mg of 64.1% sodium hydride was added to a solution of 266 mg of phenol compound (prepared in Reference Example 2) in 3 ml of dry tetrahydrofuran and stirred for ten minutes. After stirring, a solution of 264 mg of (1S,3R)-3-mesyloxycyclopentyl-carboxylic acid t-butyl ester (prepared in Reference Example 2) in hexamethylphospharamide (HMPA) was added to the solution. And the solution was stirred for three hours at 55° C.

A saturated aqueous solution of ammonium chloride was added to the reaction mixture and the mixture was extracted with ether.

The extract was washed with water and a saturated aqueous solution of sodium chloride and dried. The resude was purified by column chromatography on silica-gel (n-hexane: ethyl acetate=10:1) to give 180 mg of tert-butyl ester compound.

0.4 ml of trifluoroacetic acid was added to a solution of 180 mg of the obtained tert-butyl ester compound obtained in 2 ml of methylene chloride and the mixture was stirred for 1.5 hours.

Toluene was added to the reaction mixture. The mixture was concentrated under reduced pressure to remove excess trifluoroacetic acid.

The residue was purified by column chromatography on silica-gel (chloroform: methanol=50:1) to give 134 mg of the title compound having the following physical data.

angle of rotation: [α]$_D$+24.8 (C=1, methanol);

TLC (chloroform: methanol=10:1): Rf=0.47;

NMR: δ 7.8 (2H, d, J=8 Hz), 7.58 (1H, m), 7.45 (2H, m), 7.25 (1H, d, J=8 Hz), 6.9 (1H, d, J=8 Hz), 5.0 (1H, bs), 3.2 (1H, m);

IR (KBr tablet): ν 3300∼2500, 1690, 1660, 1580, 1460, 1440 cm$^{-1}$;

MS: m/Z 378(M+), 266.

In place of 2,3-dichloroanisole and benzoyl chloride used in Reference Example 2 as starting materials, by the same procedure as described in Reference Example 2 and Example 1, and the next compounds were used to give the compounds having the following physical data.

Relating to Example numbers 1—1 and 1-4, (1R,3S)-3-mesyloxy compound was used in place of (1S,3R)-3-mesyloxy compound used in Example 1.

And further, relating to Example numbers 1-2 and 1-4, (dl)-cis-3-mesyloxy compound was used in place of (1S,3R)-3-mesyloxy compound used in Example 1.

| Example No. | Starting materials | | Final materials | Angle of rotation $[\alpha]_D$ |
|---|---|---|---|---|
| 1 | 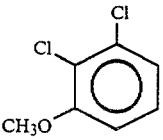 | 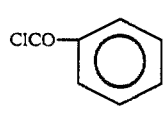 | 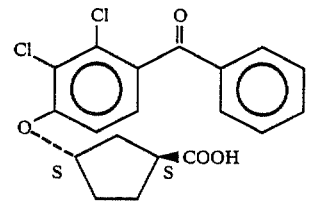 | +24.8 (C = 1, CH₃OH) |
| 1-1 | 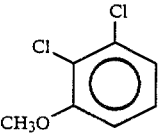 | 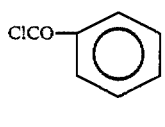 | 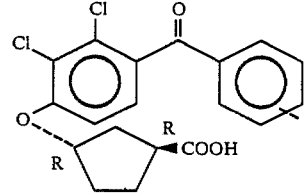 | −23.2 (C = 0.5, CH₃OH) |
| 1-2 | 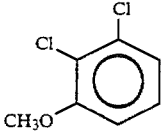 | 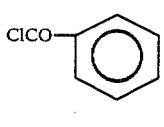 | 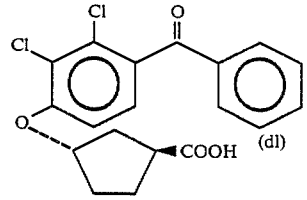 | 0 |
| 1-3 | 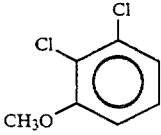 | 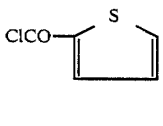 | 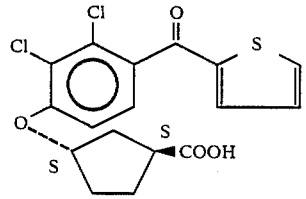 | +21.3 (C = 1, CH₃OH) |
| 1-4 | 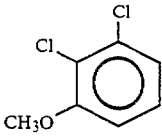 | 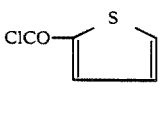 | 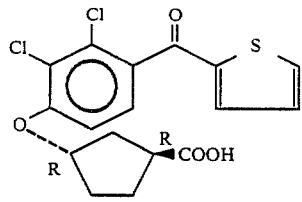 | −22.1 (C = 0.5, CH₃OH) |
| 1-5 | 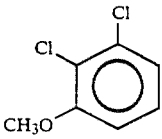 | 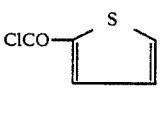 | 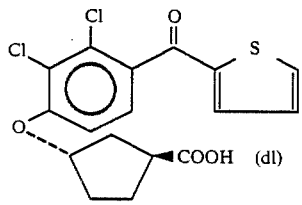 | 0 |
| 1-6 | 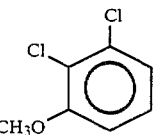 | 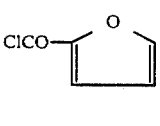 | 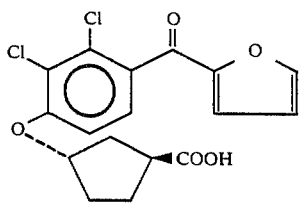 | +23.3 (C = 0.5, CH₃OH) |

-continued

| Example No. | Starting materials | | Final materials | Angle of rotation [α]$_D$ |
|---|---|---|---|---|
| 1-7 | 2,3-dichloro-methoxybenzene | 4-fluorophenyl chloroformate type (ClCO-C6H4-F) | Ketone product with cyclopentane-O, COOH and 4-F-C6H4 | +21.2 (C = 0.5, CH$_3$OH) |
| 1-8 | 2,3-dichloro-methoxybenzene | 2-fluorophenyl chloroformate | Ketone with 2-F-phenyl | +23.8 (C = 0.5, CH$_3$OH) |
| 1-9 | 2,3-dichloro-methoxybenzene | 4-methylphenyl chloroformate | Ketone with 4-CH$_3$-phenyl | +21.4 (C = 0.5, CH$_3$OH) |
| 1-10 | 2,3-dichloro-methoxybenzene | 2-methylphenyl chloroformate | Ketone with 2-CH$_3$-phenyl | +22.8 (C = 0.5, CH$_3$OH) |
| 1-11 | 2,3-dichloro-methoxybenzene | 4-nitrophenyl chloroformate | Ketone with 4-NO$_2$-phenyl | +19.6 (C = 0.5, CH$_3$OH) |
| 1-12 | 2,3-dichloro-methoxybenzene | 3-nitrophenyl chloroformate | Ketone with 3-NO$_2$-phenyl | +20.0 (C = 0.5, CH$_3$OH) |
| 1-13 | 2,3-dichloro-methoxybenzene | benzyl chloroformate | Ketone with benzyl | +21.6 (C = 0.5, CH$_3$OH) |

-continued
| Example No. | Starting materials | | Final materials | Angle of rotation $[\alpha]_D$ |
|---|---|---|---|---|
| 1-14 | 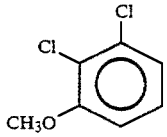 | 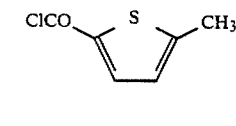 | 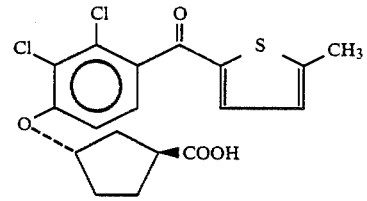 | +19.4 (C = 0.5, CH$_3$OH) |
| 1-15 | 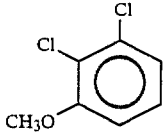 | 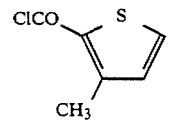 | 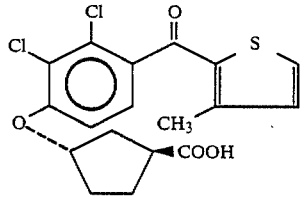 | +21.2 (C = 0.5, CH$_3$OH) |
| 1-16 | 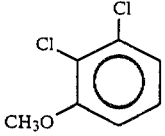 | 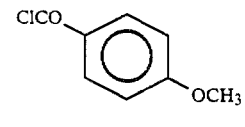 | 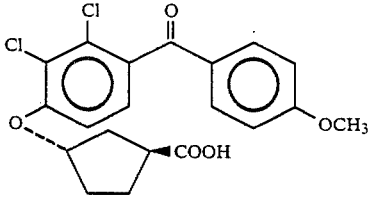 | +20.4 (C = 0.5, CH$_3$OH) |
| 1-17 | 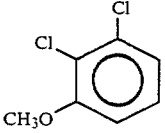 | 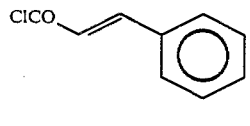 | 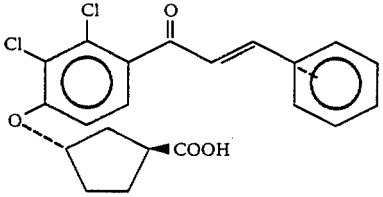 | +21.0 (C = 0.5, CH$_3$OH) |
| 1-18 | 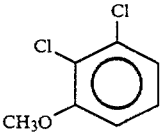 | 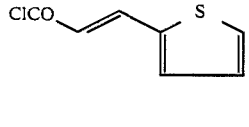 | 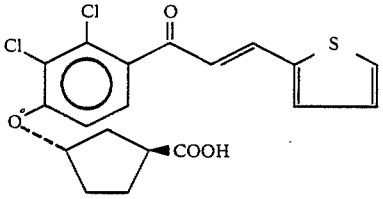 | +26.6 (C = 0.5, CH$_3$OH) |
| 1-19 | 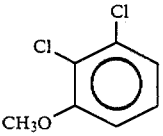 | 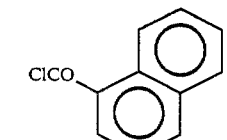 | 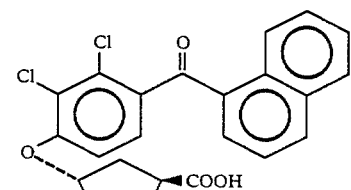 | +22.2 (C = 0.5, CH$_3$OH) |
| 1-20 | 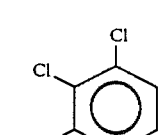 | 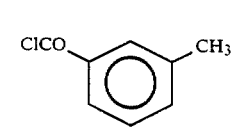 | 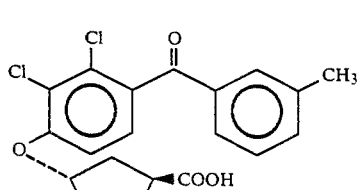 | +21.2 (C = 0.5, CH$_3$OH) |

-continued

| Example No. | Starting materials | | Final materials | Angle of rotation [α]$_D$ |
|---|---|---|---|---|
| 1-21 | 2,3-dichloro-methoxybenzene | 2-chlorophenyl chloroformate | (corresponding benzophenone cyclopentyl COOH ether) | +23.0 (C = 0.5, CH$_3$OH) |
| 1-22 | 2,3-dichloro-methoxybenzene | 2,4-dimethylphenyl chloroformate | (corresponding product) | +21.6 (C = 0.5, CH$_3$OH) |
| 1-23 | 2,3-dichloro-methoxybenzene | 2,6-dichlorophenyl chloroformate | (corresponding product) | +19.0 (C = 0.5, CH$_3$OH) |
| 1-24 | 2-chloro-methoxybenzene | phenyl chloroformate | (corresponding product) | +19.6 (C = 0.5, CH$_3$OH) |
| 1-25 | 3-chloro-methoxybenzene | phenyl chloroformate | (corresponding product) | +20.8 (C = 0.5, CH$_3$OH) |
| 1-26 | 2,6-dichlorophenyl benzoate | phenyl chloroformate | (corresponding product) | +7.4 (C = 0.5, CH$_3$OH) |
| 1-27 | 3-fluoro-methoxybenzene | phenyl chloroformate | (corresponding product) | +18.6 (C = 0.5, CH$_3$OH) |

-continued

| Example No. | Starting materials | | Final materials | Angle of rotation [α]_D |
|---|---|---|---|---|
| 1-28 | F-C6H3-OCH3 | ClCO-C6H5 | 4-F, 3-(O-cyclopentyl-COOH)-C6H3-CO-C6H5 | +17.8 (C = 0.5, CH3OH) |
| 1-29 | 2,6-(CH3)2-C6H3-OCH3 | ClCO-C6H5 | 3,5-(CH3)2-4-(O-cyclopentyl-COOH)-C6H2-CO-C6H5 | +4.8 (C = 0.5, CH3OH) |
| 1-30 | CH3O-C6H5 | ClCO-C6H3-2,4-Cl2 | 4-(O-cyclopentyl-COOH)-C6H4-CO-C6H3-2,4-Cl2 | +18.2 (C = 0.5, CH3OH) |
| 1-31 | 2,6-(CH3)2-C6H3-OCH3 | ClCO-C6H3-2,4-Cl2 | 3,5-(CH3)2-4-(O-cyclopentyl-COOH)-C6H2-CO-C6H3-2,4-Cl2 | +4.2 (C = 0.5, CH3OH) |
| 1-32 | 2,6-(CH3)2-C6H3-OCH3 | ClCO-naphthyl | 3,5-(CH3)2-4-(O-cyclopentyl-COOH)-C6H2-CO-naphthyl | +4.6 (C = 0.5, CH3OH) |
| 1-33 | 3-Cl-C6H3-OCH3 | ClCO-naphthyl | 2-Cl-4-(O-cyclopentyl-COOH)-C6H3-CO-naphthyl | +20.6 (C = 0.5, CH3OH) |

| Example No. | Starting materials | Final materials | Angle of rotation $[\alpha]_D$ |
|---|---|---|---|
| 1-34 | 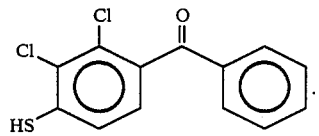 | 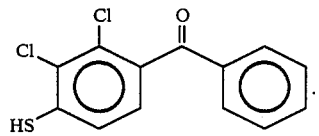 | +9.6 (C = 0.5, CH₃OH) |

The starting materials employed herein and ones employed in reference example hereafter are available in the market, known per se or may be prepared easily by conventional method.

For example, acid chloride of in example nos. 1-17 was prepared by that a cinnamic acid was allowed to react with oxalyl chloride, acid chloride of 1-18 was prepared by that 3-(2-thienyl) acrylic acid was allowed to react with an oxalyl chloride.

The benzoyl compound of 1-26 was prepared by that 2,6-dichlorophenol was allowed to react with benzoyl chloride.

Cyclopentylene groups in the compounds' name in examples after example numbers 1-6 have no RS indication. But all of them mean (1S,3S)-cyclopentylene groups.

[EXAMPLES 1-35]

(1S,3S)-[2,3-dichloro-4-(p-hydroxybenzoyl)phenoxy]-cyclopentanecarboxylic acid

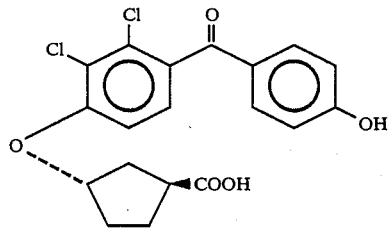

Starting material:
(1S,3S)-[2,3-dichloro-4-(p-nitrobenzoyl) phenoxy]cyclopentanecarboxylic acid tert-butyl ester
(intermediate of compound obtained by preparation of Examples 1-11).

270 mg of powder sodium hydroxide and 0.3 ml of acetoaldoxime were dissolved in 6 ml of dry dimethylformamide and the solution was cooled to 0° C.

To the solution, a solution of 719 mg of p-nitro-tert-butyl ester compound as starting material dissolved in 3 ml of dry dimethyl formamide was added dropwise. The reaction mixture brown-colored was stirred for one hour at 0° C. and for thirty minutes at room temperature. The reaction mixture was poured into 30 ml of ice-water. The mixture was adjusted with 1N-hydrochloric acid, and then the mixture was extracted with ethyl acetate.

The extract was washed with a saturated aqueous solution of sodium chloride. The solution dried and concentrated under reduced pressure.

The residue was purified by column chromatography on silica-gel (n-hexane: ethyl acetate=3:1→1:1), and 557 mg of p-hydroxy tert-butyl ester compound was obtained as brown powder.

By the same manner as the latter half procedure and purification of Example 1, with using a solution of 1 ml of trifluoroacetic acid and 135 mg of p-hydroxy-tert-butyl ester compound which obtained above dissolved in 1 ml of methylene chloride to give 105 mg of the title compound having the following physical data:

angle of rotation: $[\alpha]_D$+9.9 (C=0.5, methanol);
TLC (chloroform: methanol=10:1): Rf=0.35;
NMR (CDCl₃+CD₃OD): δ 7.70 (2H), 7:21 (1H), 6.92 (1H), 6.85 (2H), 5.00 (1H), 3.16 (1H);
IR (KBr tablet): ν 3300, 2950, 1705, 1640, 1585, 1510, 1460, 1440, 1385, 1320, 1280, 1160, 1000, 850, 820, 780, 700, 620 cm⁻¹;
MS: m/Z 394 (M+), 282.

[REFERENCE EXAMPLE 3]

Synthesis of 2,3-dichloro-4-benzoylthiophenol

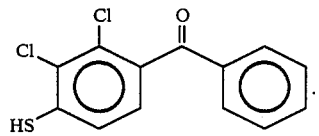

1.38 g of potassium carbonate was added to a solution of 1.0 g of 2,3-dichloro-4-benzoylphenol (prepared in Reference Example 2) in 19 ml of acetone. The mixture was stirred for twenty minutes at the room temperature. 3 ml of trifluoromethanesulfonyl chloride was dissolved in acetone and added dropwise into the mixture, and the mixture was stirred for fifteen minutes at the same temperature.

The reaction mixture was filtered off, and the filtrate was concentrate under reduced pressure. The residue was purified by column chromatography on silica-gel to give 1.39 g of trifluoro compound.

0.55 ml of thioacetic acid was added dropwise slowly at −20° C. to a solution of 260 mg of 63% sodium hydride dissolved in 10 ml of dimethylformamide.

The mixture was stirred for thirty minutes and then 1.39 g of trifluoro compound in 5 ml of dimethylformamide was added slowly to the mixture and stirred for thirty minutes at the same temperature and for thirty minutes at 0° C. and further for one hour at room temperature.

The reaction mixture was poured into 30 ml of an aqueous solution of ammonium chloride and the mixture was extracted ether. The extract was dried and concentrated under reduced pressure.

The residue was purified by column chromatography on silica-gel (n-hexane: ethyl acetate=10:1) to give 200 mg of thioester compound.

100 mg of sodium hydroxide was added to a mixed solvent of 0.8 ml of water and 6 ml of methanol. 200 mg of thioester compound was added to the above solution. The mixture was stirred for 1.5 hours at room temperature.

The reaction mixture was concentrated under reduced pressure, and 15 ml of 1N hydrochloric acid was added to and the mixture was extracted with ethyl acetate.

The extract was dried and concentrated under reduced pressure. The residue was purified by column chromatography (n-hexane: ethyl acetate=3:1) to give 166 mg of the title compound.

[EXAMPLE 2]

(1S,3S)-3-[4-benzoyl-2,3-dichlorophenylthio]cyclopentanecarboxylic acid

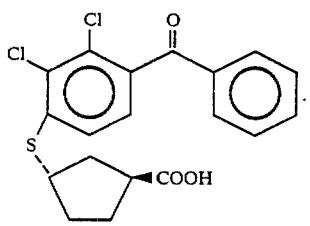

By the same procedure as described in Example 1, the title compound having the following physical data was obtained from thiophenol compound prepared in Reference Example 3.

angle of rotation: $[\alpha]_D$ −0.6 (C=0.5, methanol);
TLC (chloroform: methanol=10:1): Rf=0.45;
NMR: δ 7.80 (2H, m), 7.60 (1H, m), 7.46 (2H, m), 7.25 (2H, t), 3.88 (1H, m), 3.15 (1H, m);
IR (KBr tablet): ν 3,400, 2950, 1700, 1665, 1590, 1570, 1440, 1360, 1315, 1280, 1190, 1170, 1135, 960, 800, 760, 730, 700 cm$^{-1}$;
MS: m/Z 394(M+), 282.

[EXAMPLE 3]

(1S,3S)-3-(2,3-dichloro-4-benzoylphenoxy)-1-(tetrazol-5′-yl)cyclopentane

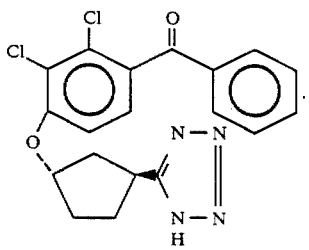

In an atmosphere of argon, 5 ml of oxalyl chloride was added to 1.11 g of (1S,3S)-3-[(2,3-dichloro-4-benzoyl)phenoxy]cyclopentanecarboxylic acid (prepared in Example 1) and the mixture was stirred for one hour at room temperature.

The mixture solution was concentrated under reduced pressure to distill off excess oxalyl chloride.

The residue was dissolved in 1,4-dioxane and the solution cooled to 0° C., 10 ml of ammonia water was added to and the mixture was stirred for one hour at same temperature and further stirred for over night at room temperature.

The reaction mixture was concentrated under reduced pressure to distill off ammonia water.

The concentrated residue was filtered off and washed with water to except ammonium chloride, and them dried to give 1.0 g of amide compound.

1 ml of thionyl chloride was added to a solution of 1.0 g of amide compound in 5 ml of dimethylformamide. The mixture was stirred for two hours at 80° C.

The reaction mixture was poured into 50 ml of ice-water, and the mixture was alkalized by employing 50% an aqueous solution of potassium hydroxide, and the mixture was extracted with ether.

The extract was washed with water and dried and concentrated under reduced pressure. The residue obtained was purified by column chromatography on silica-gel (ethyl acetate: n-hexane=1:2) to give 840 mg of nitrile compound.

134 mg of ammonium chloride and 163 mg of sodium azide were added to 150 mg of nitrile compound in 3 ml dimethylformamide. The mixture was stirred for forty-eight hours at 140° C.

The reaction mixture was poured into 20 ml of ice-water. The mixture was acidified with hydrochloric acid and the mixture was extracted with ethyl acetate.

The extract was washed with water and dried and concentrated under reduced pressure. The residue obtained was purified by column chromatography on silica-gel (chloroform: methanol=50:1) to give 109 mg of the title compound having the following physical data.

angle of rotation: $[\alpha]_D$ +29.8 (C=0.5, methanol);
TLC (methanol: chloroform=1:10): Rf=0.30;
NMR (CDCl$_3$+CD$_3$CD): δ 7.80 (2H, m), 7.60 (1H, m), 7.46 (2H, m), 7.28 (1H, d, J=8 Hz), 6.96 (1H, d, J=8 Hz), 5.12 (1H, br), 3.80 (1H, m);
IR (KBr tablet): ν 3450, 1660, 1580, 1540, 1460, 1140, 1380, 1315, 1285, 1265, 1160, 1010, 820 cm$^{-1}$;
MS: m/Z 402(M+), 359, 266.

[REFERENCE EXAMPLE 4]

4-benzoylnaphthol

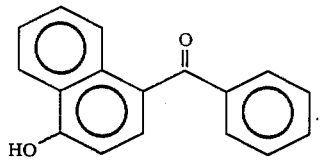

5 g of 4-methoxy-1-naphthylaldehyde was dissolved in 30 ml of dry ether and 25 ml of dry tetrahydrofuran.

The ethereal solution of phenylmagnesium bromide, which was prepared from bromobenzene and magnesium, was added at 0° C., until 4-methoxy-1-naphthylaldehyde as the starting material was disappeared.

The reaction mixture was stirred for thirty minutes at the same temperature and poured into 100 ml of an aqueous solution of ammonium chloride, and further the solution was extracted with ethyl acetate. The extract was washed with water and dried and concentrated under reduce pressure, and the residue was purified by column chromatography on silica-gel (ethyl acetate: n-hexane=1:3) to give 6.44 g of alcohol compound.

Jone's reagent was added to a solution of 966 mg of alcohol compound dissolved in 20 ml of acetone at 0° C.

until alcohol compound as the starting material was disappeared.

The reaction mixture was stirred for one hour at the same temperature, and about 10 ml of acetone was distilled off and 20 ml of ethyl acetate and 20 ml of water was added to and the mixture was shaked.

The mixture was divided water layer and organic layer, and the organic layer was dried and concentrated under reduced pressure.

The residue was purified by column chromatography on silica-gel (ethyl acetate: n-hexane=1:5) to give 1.25 g of ketone compound.

1.25 g of the ketone compound was reacted with 10% pyridium chloride, and the crude product was purified by recrystallization from benzene to obtain 715 mg of the title compound.

[REFERENCE EXAMPLE 4(a)]

2,3-dimethyl-4-benzoylphenol

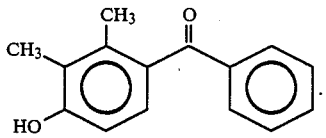

By the same procedure as described in Reference Example 4, the title compound was obtained from 2,3-dimethyl-4-methoxybenzaldehyde.

By the same procedure as described in Example 1, and obtained the compounds of Examples 4 and 4(a) having the following physical data.

[EXAMPLE 4]

(1S,3S)-3-(4-benzoyl-1-naphthoxy)cyclopentanecarboxylic acid

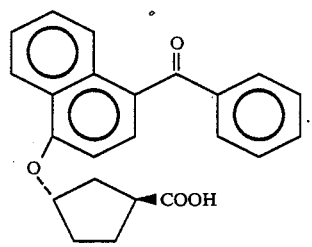

starting material: 4-benzoylnaphthol (prepared in Reference Example 4);
angle of rotation: $[\alpha]_D + 25.0$ (C=0.5, methanol);
TLC (chloroform: methanol=10:1): Rf=0.50;
NMR: δ 8.40~8.24 (2H, m), 7.88~7.70 (2H, m), 7.64~7.40 (6H, m), 6.77 (1H, d), 5.16 (1H, br), 3.25 (1H, m);
IR (KBr tablet): ν 3450, 3100~2000, 1705, 1645, 1575, 1510, 1460, 1445, 1430, 1330, 1290, 1250, 1160, 1080, 1050, 1020, 825, 800, 770, 720, 700, 660 cm$^{-1}$;
MS: m/Z 360(M+), 248.

[EXAMPLE 4(a)]

(1S,3S)-3-[(2,3-dimethyl-4-benzoyl)phenoxy]cyclopentanecarboxylic acid

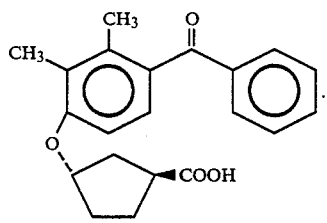

starting material: 2,3-dimethyl-4-benzoylphenol (prepared in Reference Example 4(a));
angle of rotation: $[\alpha]_D + 21.2$ (C=0.5, methanol);
TLC (chloroform: methanol=10:1): Rf=0.50;
NMR: δ 7.80 (2H, m), 7.60~7.38 (3H, m), 7.14 (1H, d), 6.69 (1H, d), 4.94 (1H, br), 3.18 (1H, m);
IR (KBr tablet): ν 3430, 2930, 1690, 1590, 1480, 1450, 1360, 1320, 1290, 1260, 1190, 1170, 1090, 1050, 1020, 995, 965, 820, 800, 755, 715 cm$^{-1}$;
MS: m/Z 338(M+), 225.

[REFERENCE EXAMPLE 5]

2,3-dichloro-4-diphenylcarbamoylphenol

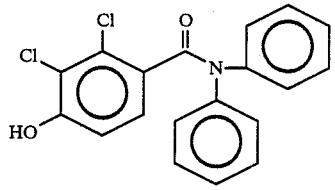

19.1 ml of an aqueous solution of titanium tetrachloride was added dropwise to 18.5 g of 2,3-dichloroanisole (on the market) in 50 ml of methylene chloride, and then 7.9 ml of α,α-dichloromethyl methyl ether was added to this solution.

The reaction mixture was stirred for 20 minutes at the room temperature and poured into 150 g of ice and the mixture was extracted with methylene chloride.

The extract was washed with water and an aqueous solution of sodium hydrocarbonate, dried and concentrated under reduced pressure to give 23.5 g of aldehyde compound.

A solution of 25.4 g of potassium permanganate in 510 ml of water was added to a suspension of 23.5 g of the aldehyde prepared above in 300 ml of water at room temperature.

The reaction mixture was stirred for 1 hour at 75° C., and 50 ml of a 10% aqueous solution of sodium hydroxide was added, and manganese dioxide was filtered off.

The filtrate was cooled to 0° C. and acidified with hydrochloric acid, and the precipitation was filtered and washed with cool-water.

The solids obtained was purified by recrystallization from methanol to obtain 6.85 g of carboxylic acid.

In an atmosphere of argon, 0.8 ml of acetone and 2 ml of oxalyl chloride were added to 440 mg of obtained carboxylic acid and stirred for 2 hours at 40° C.

Excess acetone and oxalyl chloride was distilled off under reduced pressure to obtain acid chloride and cooled to 0° C., 406 mg of diphenylamine and 2 ml of pyridine was added dropwise to a 0° C.-cooled solution of acid chloride obtained in 5 ml of methylene chloride.

The reaction mixture was stirred for 30 minutes at 0° C. and for 1 hour at room temperature, and poured into 30 ml of 1N hydrochloric acid and the mixture was acidified with concentrated hydrochloric acid.

The solution was extracted with ethyl acetate, the extract was washed with an aqueous solution of sodium hydrocarbonate and an aqueous solution of sodium chloride and dried and concentrated under reduced pressure.

The residue was purified by Lobar column (registered Trade Mark) (ethyl acetate: n-hexane=1:2) to give 475 mg of. amido compound.

475 mg of amido compound was reacted with 3.5 g of pyridine hydrochloride and purified by column chromatography on silica-gel (chloroform: methanol=20:1) to give 364 mg of alcohol compound.

NMR: δ 7.40~7.00 (11H, m), 6.70 (2H, d, J=8 Hz), 5.73 (1H, S);
MS: m/Z 357(M+).

[REFERENCE EXAMPLE 5(a)]

2.3-dichloro-4-phenylcarbamoylphenol

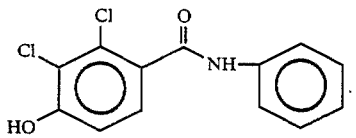

By the same procedure as described in Reference Example 5, using aniline in place of diphenylamine to give the title compound.

starting material: the same as described in Reference Example 5;
NMR: δ 7.80 (1H, br), 7.62 (3H, m), 7.37 (2H, t, J=8 Hz), 7.18 (1H, d, J=8 Hz), 6.91 (1H, d, J=8 Hz), 5.70 (1H, S);
MS: m/Z 281(M+)

By the same procedure as described in Example 1, compounds of Examples 5 and 5(a) having the following physical data.

[EXAMPLE 5]

(1S,3S)-3-(2,3-dichloro-4-diphenylcarbamoylphenoxy)-cyclopentanecarboxylic acid

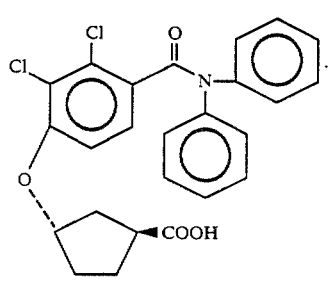

starting material: 2,3-dichloro-4-diphenylcarbamoylphenol (prepared in Reference Example 5);
angle of rotation: [α]_D+17.0 (C=0.5, methanol);
TLC (chloroform: methanol=10:1): Rf=0.45;
NMR: δ 7.50~7.00 (11H, br), 6.69 (1H, d), 4.86 (1H, br), 3.15 (1H, m);

IR (KBr tablet): ν 3400, 2900, 1700, 1650, 1580, 1485, 1460, 1340, 1280, 1160, 1090, 810, 750, 690 cm$^{-1}$;
MS: m/Z 469(M+), 301.

[EXAMPLE 5(a)]

(1S,3S)-3-(2,3-dichloro-4-phenylcarbamoylphenoxy)cyclopentanecarboxylic acid

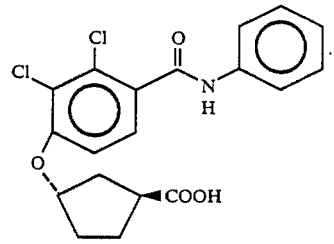

starting material: 2,3-dichloro-4-phenoxycarbamoylphenol (prepared in Reference Example 5(a));
angle of rotation: [α]_D+25.2 (C=0.5, methanol);
TLC (chloroform: methanol=10:1): Rf=0.45;
NMR (CDCl$_3$+CD$_3$OD): δ 7.65~7.54 (3H, m), 7.42~7.32 (2H, m), 7.20~7.11 (1H, m), 6.93 (1H, d), 4.98 (1H, br), 3.14 (1H, br);
IR (KBr tablet): ν 3270, 3150~2200, 1685, 1650, 1520, 1490, 1460, 1435, 1380, 1320, 1265, 995, 750 cm$^{-1}$;
MS: m/Z 393(M+).

By the same procedure as described in Example 1, compounds of Examples 6 and 6(a) were obtained.

[EXAMPLE 6]

(1S,3S)-3-(4-benzoylphenoxy)cyclopentanecarboxylic acid

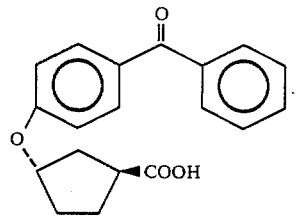

starting material: p-hydroxybenzophenone;
angle of rotation: [α]_D+20.4 (C=0.5, methanol);
TLC (chloroform: methanol=10:1): Rf=0.57;
NMR: δ 7.8 (2H, d, J=8 Hz), 6.9 (2H, d, J=8 Hz), 4.95 (1H, br), 3.1 (1H, m);
IR: ν 2500, 1730, 1700, 1640, 1590, 1500 cm$^{-1}$;
MS: m/Z 310(M+). 198.

[EXAMPLE 6(a)]

(1S,3S)-3-[4-(2-thenoyl)phenoxy]cyclopentanecarboxylic acid

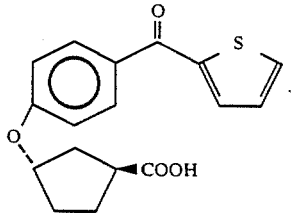

starting material: 4-(2-thiophenecarbonyl)phenol;
angle of rotation: $[\alpha]_D +21.4$ (C=0.5, methanol);
TLC (chloroform: methanol=10:1): Rf=0.40;
NMR: δ 7.88 (2H, d, J=8 Hz), 7.7~7.6 (2H, dd, dd), 7.15 (1H, dd), 6.92 (2H, d, J=8 Hz), 4.97 (1H, bs), 3.2~3.0 (1H, m);
IR: ν 3500~2500, 1700, 1620, 1590, 1500 cm$^{-1}$.

[EXAMPLE 7]

500 mg of (1S,3S)-3-[(2,3-dichloro-4-benzoyl)phenoxy]cyclopentanecarboxylic acid (prepared in Example 1) was dissolved in 5 ml of ethanol and the solution was sterilized by filtration through a bacteria-retaining filter, and placed 0.1 ml portions into 1 ml ampoules to obtain ampoules each containing 10 mg of the active ingredient, and the ampoules were then sealed.

The contents of ampoules are used for injection by diluting with a suitable quantity of dilution, for example, by diluting with a tris-hydrochloric acid buffer solution (pH 8.6) to 1 ml.

What is claimed is:

1. A 3-(4-aroyl)phenoxy cyclopentanecarboxylic acid derivative represented by the general formula:

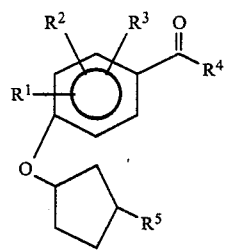

where $R^1$, $R^2$ and $R^3$ represent a hydrogen atom or a halogen atom, with the proviso that when two or three of $R^1$, $R^2$ and $R^3$ represent halogen atoms, they represent the same atoms, $R^4$ represents the general formula:

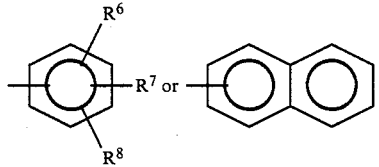

wherein $R^6$, $R^7$ and $R^8$ represents a hydrogen atom or a halogen atom, with the proviso that when two or three of $R^6$, $R^7$ and $R^8$ represent halogen atoms, they represent the same atoms, $R^5$ represents a 5-tetrazolyl group or a carboxy group, or a non-toxic salt thereof.

2. A derivative according to claim 1, wherein $R^4$ represents a group of the formula:

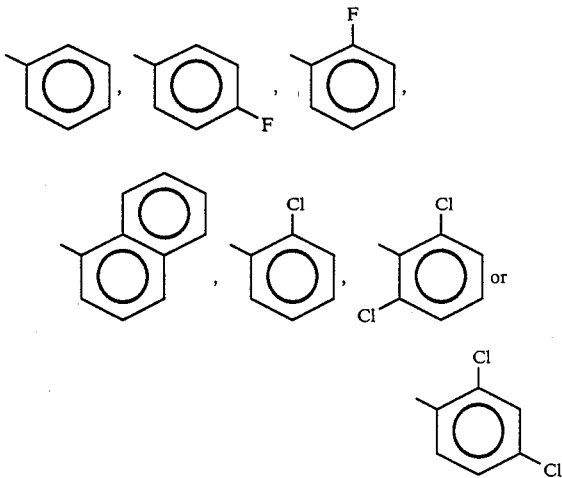

3. A derivative according to claim 1, which is (1S,3S)-3-((2,3-dichloro-4-benzoyl)phenoxy)cyclopentanecarboxylic acid.

4. A derivative according to claim 1, which is (1S,3S)-3-[{2,3-dichloro-4-(2-fluorobenzoyl)}phenoxy]cyclopentanecarboxylic acid, (1S,3S)-3-[{2,3-dichloro-4-(1-naphthoyl)}phenoxy]cyclopentanecarboxylic acid, (1S,3S)-3-[(3-chloro-4-benzoyl)phenoxy]cyclopentanecarboxylic acid, (1S,3S)-3-(2,3-dichloro-4-benzoyl phenoxy)-1-(tetrazol-5′-yl)cyclopentane or a non-toxic salt thereof.

5. A pharmaceutical composition for the prevention and/or the treatment of cerebral edema, which comprises, as active ingredient, an effective amount of the compound of general formula (I) depicted in claim 1 or a non-toxic salt thereof, together with a pharmaceutical carrier and/or coating.

6. A method for the prevention and/or treatment of cerebal edema, which comprises administering to the patient an effective amount of the compound of general formula (I) of claim 1 or a non-toxic salt thereof.

* * * * *